United States Patent [19]
Doehner, Jr. et al.

[11] Patent Number: 5,625,082
[45] Date of Patent: Apr. 29, 1997

[54] 2-ARYL-5-(TRIFLUOROMETHYL)-2-PYRROLINE COMPOUNDS USEFUL IN THE MANUFACTURE OF INSECTICIDAL, NEMATOCIDAL AND ACARICIDAL ARYLPYRROLES

[75] Inventors: Robert F. Doehner, Jr.; Jerry M. Barton, both of East Windsor, N.J.; David G. Kuhn, Newtown, Pa.

[73] Assignee: American Home Products Corporation, Madison, N.J.

[21] Appl. No.: 333,827

[22] Filed: Nov. 3, 1994

Related U.S. Application Data

[62] Division of Ser. No. 156,332, Nov. 22, 1993, Pat. No. 5,380,876, which is a division of Ser. No. 865,149, Apr. 8, 1992, Pat. No. 5,288,901, which is a division of Ser. No. 634,287, Dec. 26, 1990, Pat. No. 5,118,816.

[51] Int. Cl.$^6$ .................. C07D 317/48; C07C 231/10
[52] U.S. Cl. .................. 549/441; 564/123; 564/133; 564/142
[58] Field of Search ............... 549/441; 564/123, 564/133, 142

[56] References Cited

U.S. PATENT DOCUMENTS

| | | | |
|---|---|---|---|
| 3,412,154 | 11/1968 | Fleming | 548/565 |
| 3,468,952 | 9/1969 | Ehrhart et al. | 562/449 |
| 3,644,414 | 2/1972 | Helsley et al. | 548/565 |
| 4,485,243 | 11/1984 | Vander Stol et al. | 548/565 |
| 4,594,429 | 6/1986 | Ueda et al. | 548/565 |
| 4,680,413 | 7/1987 | Genda et al. | 548/565 |
| 4,778,901 | 10/1988 | Martin | 548/565 |
| 5,151,536 | 9/1992 | Kameswaren et al. | 548/531 |

FOREIGN PATENT DOCUMENTS

| | | | |
|---|---|---|---|
| 1470386 | 3/1969 | Germany | 548/565 |

OTHER PUBLICATIONS

Martin et al., "2-Phenylaspartic Acid Derivatives from Beta-Lactams," *J. Org. Chem.*, 35(11), pp. 3814–3818, (1970).

*Primary Examiner*—David B. Springer
*Attorney, Agent, or Firm*—Peggy A. Climenson

[57] ABSTRACT

There is provided a process for preparing intermediates having the structure

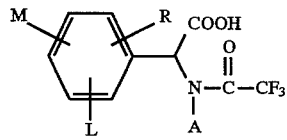

from the corresponding aldehydes having the structure

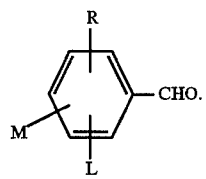

7 Claims, No Drawings

2-ARYL-5-(TRIFLUOROMETHYL)-2-PYRROLINE COMPOUNDS USEFUL IN THE MANUFACTURE OF INSECTICIDAL, NEMATOCIDAL AND ACARICIDAL ARYLPYRROLES

This is a divisional of application Ser. No. 08/156,332 filed on Nov. 22, 1993 U.S. Pat. No. 5,380,876, which is a divisional of application Ser. No. 07/865,149 filed on Apr. 8, 1992, now U.S. Pat. No. 5,288,901 which is a divisional of application Ser. No. 07/634,287, filed on Dec. 26, 1990, now U.S. Pat. No. 5,118,816.

BACKGROUND OF THE INVENTION

Certain substituted arylpyrrole compounds and their use as insecticidal, acaricidal and nematocidal agents are described in copending U.S. application Ser. No. 392,495 filed on Aug. 11, 1989 which is a continuation-in-part of U.S. application Ser. No. 208,841 filed on Jun. 23, 1988 which is a continuation-in-part of U.S. application Ser. No. 079,545 filed on Jul. 29, 1987, now abandoned. A process for the preparation of 2-aryl-5-(trifluoromethyl)pyrrole compounds via an azalactone intermediate is described in copending U.S. application Ser. No. 560,396 filed on Jul. 31, 1990.

It is an object of this invention to present more useful intermediates for the process of manufacture of a variety of insecticidal, acaricidal and nematocidal arylpyrrole compounds and a method for the preparation of said intermediates. Methods for the use of the pyrroline and glycine intermediates of the present invention in the process of manufacture of arylpyrrole insecticidal agents is described in copending U.S. application Ser. No. 07/634,287, now U.S. Pat. No. 5,118,816, filed concurrently herewith and incorporated herein by reference thereto.

SUMMARY OF THE INVENTION

The present invention relates to compounds of formula I

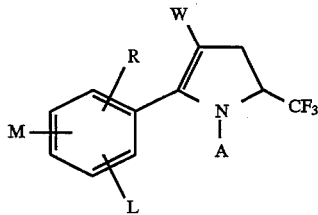

wherein

A is hydrogen or $C_1$–$C_4$ alkyl;

W is CN, $NO_2$ or $CO_2R_6$;

L is hydrogen or halogen and

M and R are each independently hydrogen, $C_1$–$C_4$ alkyl, $C_1$–$C_4$ alkoxy, $C_1$–$C_4$ alkylthio, $C_1$–$C_4$ alkylsulfinyl, $C_1$–$C_4$ alkylsulfonyl, cyano, nitro, halogen, $CF_3$, $R_1CF_2Z$, $R_2CO$ or $NR_3R_4$ and when M and R are on adjacent positions they may be taken together with the carbon atoms to which they are attached to form a ring in which MR represents the structure —$OCH_2O$—, —$OCF_2O$— or —CH=CH—CH=CH—;

Z is $S(O)_n$ or O;

$R_1$ is hydrogen, F, $CHF_2$, CHFCl or $CF_3$;

$R_2$ is $C_1$–$C_4$ alkyl, $C_1$–$C_4$ alkoxy or $NR_3R_4$;

$R_3$ is hydrogen or $C_1$–$C_4$ alkyl;

$R_4$ is hydrogen, $C_1$–$C_4$ alkyl or $R_5CO$;

$R_5$ is hydrogen or $C_1$–$C_4$ alkyl and $R_6$ is $C_1$–$C_6$ alkyl, $C_3$–$C_6$ cycloalkyl or phenyl;

n is an integer of 0, 1 or 2.

The present invention also relates to compounds of formula II

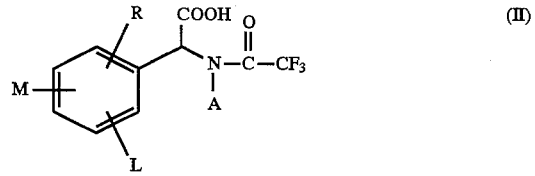

wherein A, L, M and R are as describe above for formula I with the proviso that when A is hydrogen, then at least one of L, M and R must be other than hydrogen.

This invention further relates to a method for the preparation of the above compounds and their use in the manufacture of arylpyrrole insecticidal agents.

DESCRIPTION OF THE INVENTION

Compounds of formula I may be prepared by reacting compounds of formula II with about 1.0 molar equivalent of an activated olefin of formula III $$H_2C=CHW \qquad (III)$$

wherein W is CN, $NO_2$ or $CO_2R_6$ and $R_6$ is $C_1$–$C_6$ alkyl, $C_3$–$C_6$ cycloalkyl or phenyl in the presence of an acid anhydride and a solvent, optionally in the presence of an organic base. The method of preparation is illustrated in Flow Diagram I.

FLOW DIAGRAM I

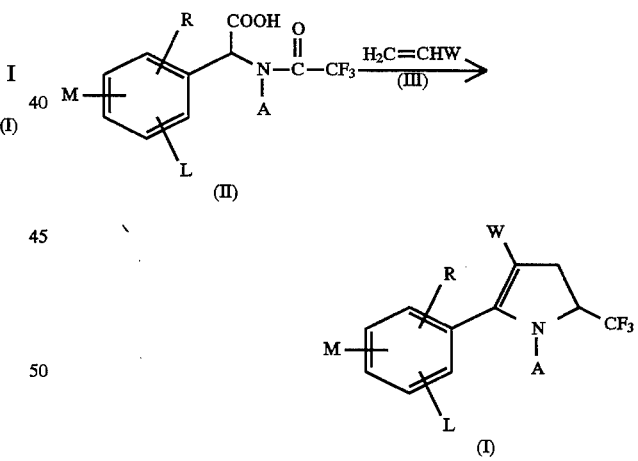

Solvents that may be used in the method of invention include aprotic organic solvents for example nitriles such as acetonitrile; esters such as ethyl acetate, methyl propionate and the like; ethers such as diethyl ether, tetrahydrofuran, dioxane, ethylene glycol dimethyl ether and the like; halogenated hydrocarbons such as methylene chloride, 1,2-dichloroethane, chloroform, 1,1,1-trichloroethane, carbon tetrachloride and the like; carboxylic acid amides such as N,N-dimethylformamide, N-methylpyrrolidinone and the like; sulfoxides such as dimethyl sulfoxide; sulfones such as tetramethylene sulfone; aromatic hydrocarbons such as benzene, toluene, xylene and the like; halogenated aromatic hydrocarbons such as chlorobenzene, o-dichlorobenzene and the like. One of the preferred organic solvents is acetontrile. Acid anhydrides suitable for use in the method of invention are lower-alkyl anhydrides such as acetic anhydride. Among the organic bases that may be used in the invention method are pyridine, morpholine, tri($C_1$–$C_4$) alkylamine, hexamethylenetetramine, dimethylamino pyridine and the like. A preferred organic base is a tri($C_1$–$C_4$) alkylamine such as triethylamine.

Compounds of formula II may be prepared from the appropriate arylaldehyde and suitable amine precursor via a Strecker synthesis to form the amino acid intermediate of formula III which may be trifluoroacetylated to obtain the desired formula II compound as shown in Flow Diagram II.

FLOW DIAGRAM II

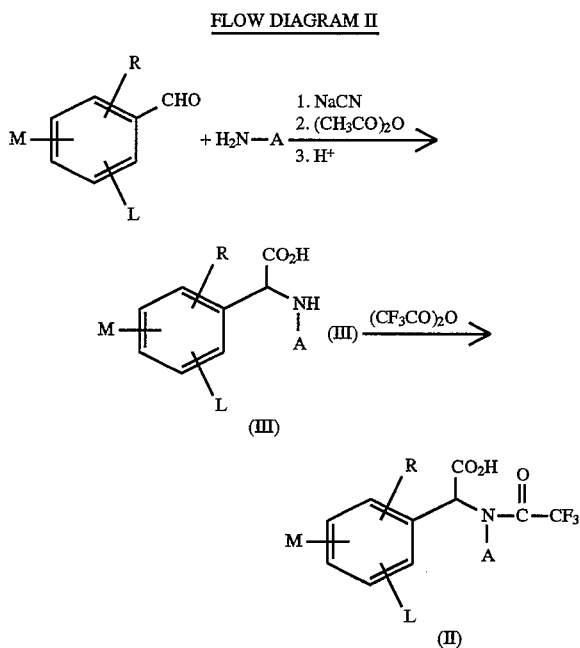

Compounds of formula II wherein A is hydrogen may also be prepared via trifluoroacetylation of the appropriate arylglycine precursor. Alkylation of the thus-obtained compound using an alkylating agent such as a lower alkylhalide gives compounds of formula II wherein A is $C_1$–$C_4$ alkyl. Using methyl iodide as the alkylating agent, the reaction sequence is illustrated in flow diagram III.

FLOW DIAGRAM III

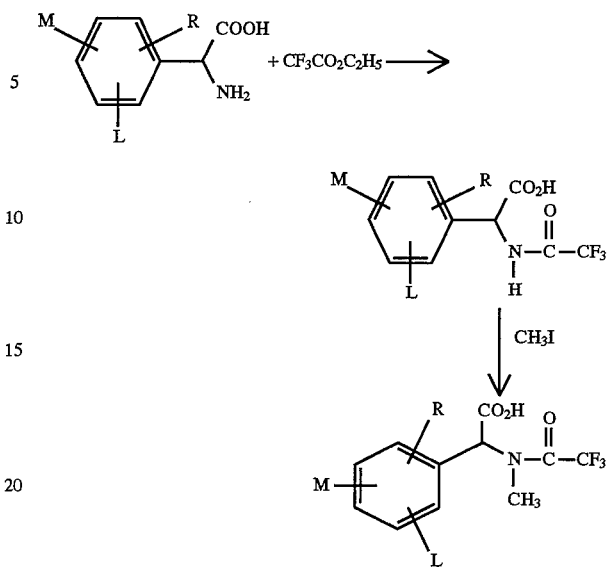

The compounds of the invention are intermediates in the manufacture of a variety of arylpyrroles useful as insecticidal, nematocidal and acaricidal agents. Among the arylpyrrole insecticidal agents that may be prepared from the compounds of the invention are 4-halo-2-(p-chlorophenyl)-1-(substituted)-5-(trifluoromethyl)pyrrole-3-carbonitrile compounds. In one example of the method of the invention, the formula I pyrroline compound wherein A is methyl, W is CN, L and R are hydrogen and M is Cl may be reacted with a halogen in the presence of an aprotic solvent at an elevated temperature to give insecticidal arylpyrrole agents of formulas IV and V wherein X is chlorine, bromine or iodine. Further reaction with additional halogen in the presence of a radical initiator such as benzoyl peroxide, 2,2'-azobisisobutyronitrile, photochemical irradiation and the like yields the corresponding 1-(halomethyl)pyrrole intermediate of formula VI which can be reacted with an alkali metal alkoxide such as sodium ethoxide, potassium methoxide or the like to given an arylpyrrole insecticidal agent of formula VII. The reaction are shown in Flow Diagram IV.

FLOW DIAGRAM IV

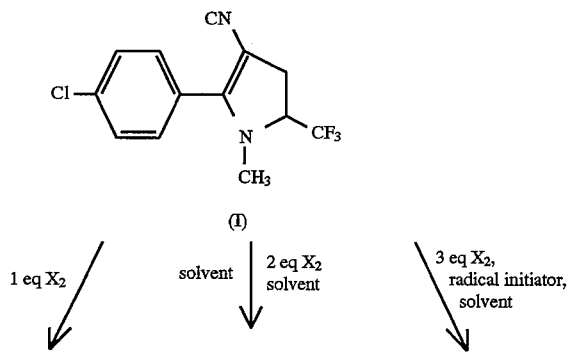

-continued
FLOW DIAGRAM IV

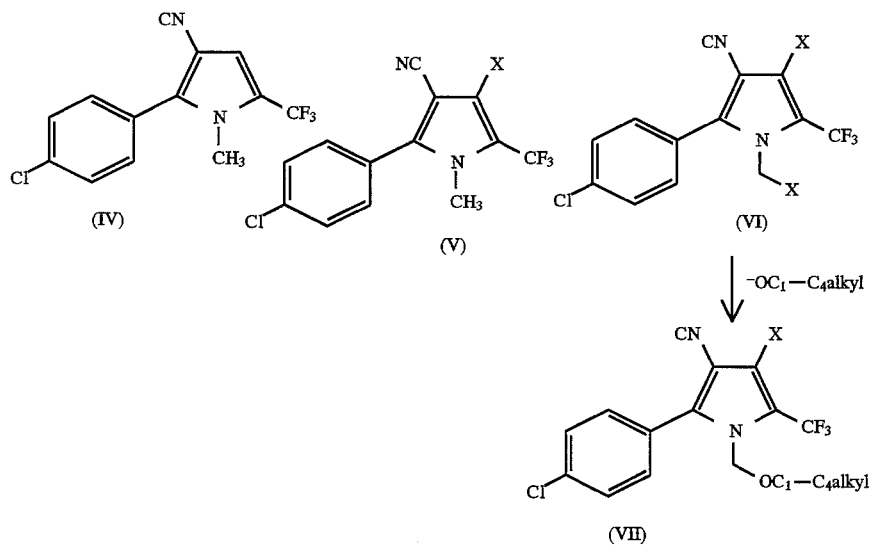

By varying the substituents A, W, L, M and R, the halogen reactant and the reaction conditions, a wide variety of arylpyrrole insecticidal, nematocidal and acaricidal agents may be manufactured from the compounds of formula I.

In order to facilitate a further understanding of the invention, the following examples are presented to illustrate more specific details thereof. The invention is not to be limited thereby except as defined in the claims. The term NMR designates nuclear magnetic resonance and the term HPLC designates high pressure liquid chromatography. Unless otherwise noted, all parts are parts by weight.

EXAMPLE 1

Preparation of 2-(p-Chlorophenyl)sarcosine

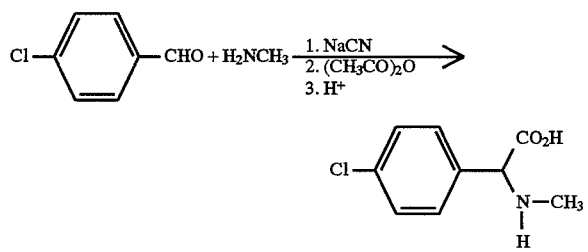

A mixture of p-chlorobenzaldehyde (153 g, 1.0 mol) in tetrahydrofuran is treated with a solution of methylamine hydrochloride (88 g, 1.3 mol) in water followed by an aqueous solution of sodium cyanide (53 g, 1.0 mol), stirred at room temperature for 16 hours and extracted with toluene. The organic extract is treated with 10 cc of pyridine followed by 50 cc of acetic anhydride (exotherm), stirred at ambient temperatures for ½ hour and concentrated in vacuo to give an oil residue. The residue is added to a 1:1 mixture of water and concentrated hydrochloric acid, heated at reflux temperature for 2 hours, cooled, diluted with water and neutralized to about pH 2 with 50% NaOH solution. The resultant solid precipitate is filtered and air-dried to give the title product as a white solid, 180 g (89.5% yield), mp 208°–213° C.

EXAMPLE 2

Preparation of 2-(p-Chlorophenyl)-N-(trifluoroacetyl)sarcosine

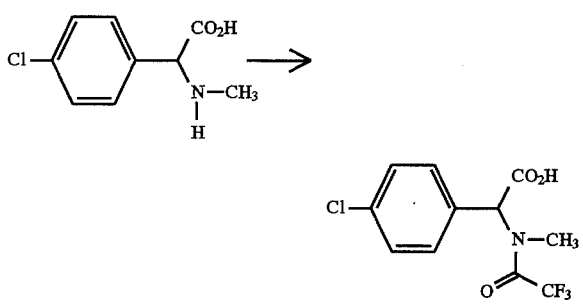

A mixture of 2-(p-chlorophenyl)sarcosine (27 g, 0.135 mol) in dry toluene is treated with 20 cc of trifluoroacetic anhydride, stirred for 1 hour and concentrated in vacuo to give a solid residue. The residue is re-evaporated several times with toluene to give the title product as a red solid, 38.7 g (97% yield), mp 117°–118° C., identified by NMR spectroscopy.

EXAMPLE 3

Preparation of 2-phenyl-N-(trifluoroacetyl)glycine

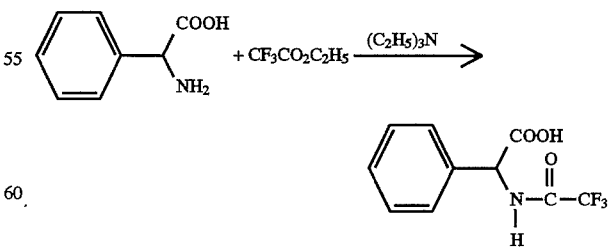

A mixture of DL-phenylglycine (15.1 g, 0.10 mol) in methanol is treated with triethylamine (10.1 g, 0.10 mol) and ethyl trifluoroacetate (17.8 g, 0.125 mol), stirred at room temperature for 72 hours, diluted with methanol and treated with Dowex 50×8 acidic resin. The reaction mixture is stirred for 10 minutes and filtered. The filtrate is concentrated in vacuo to give a pale yellow solid which is recrystallized from 1,2-dichloroethane to give the title product as white needles, 10.5 g (42% yield), mp 155°–157° C.

EXAMPLE 4

Preparation of 2-p-chlorophenyl-N-(trifluoroacetyl)glycine

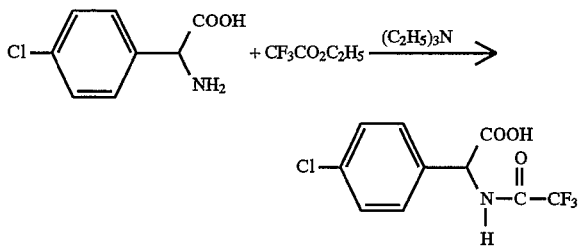

A mixture of 2-(p-chlorophenyl)glycine (37.1 g, 0.2 mol) in methanol is treated with triethylamine (20.2 g, 0.2 mol), stirred for 10 minutes, treated dropwise with ethyl trifluoroacetate (35.5 g, 0.25 mol), stirred for 4 days, diluted with methanol and treated with Dowex 50×8-100 ion exchange resin. The reaction mixture is stirred for 10 minutes and filtered. The filter cake is washed with methanol. The filtrates are combined and concentrated in vacuo to afford a yellow solid which is recrystallized from 1,2-dichloroethane to give the title compound as white crystals, 26.4 g (46.8% yield, mp 170°–172° C.

EXAMPLE 5

Preparation of 2-Phenyl-N-(trifluoroacetyl)sarcosine

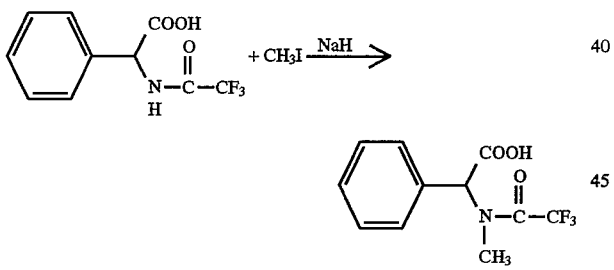

A mixture of 2-phenyl-N-(trifluoroacetyl)glycine (2.5 g, 0.01 mol) and iodomethane (11.35 g, 0.08 mol) in tetrahydrofuran is treated portionwise with a 60% dispersion of sodium hydride in mineral oil (1.2 g, 0.03 mol NaH), stirred at ambient temperatures for 1 hour, heated at reflux temperature for 17 hours, cooled to room temperature, diluted with ethyl acetate followed by 1 ml of water and concentrate in vacuo to a wet yellow solid residue. The residue is dispersed in a mixture of ether and water. The ether layer is washed with a sodium bicarbonate solution. The aqueous phases are combined, acidified with 10% HCl and extracted with ethyl acetate. The ethyl acetate extract is washed sequentially with water, sodium thiosulfate and saturated sodium chloride solution, dried over $MgSO_4$ and concentrated in vacuo to give a pale yellow solid which is recrystallized from methylcyclohexane to give the title compound as white crystal, 0.5 g, (19.1% yield), mp 124°–126° C.

EXAMPLE 6

Preparation of 2-(p-Chlorophenyl)-1-methyl-5-trifluoromethyl)-2-pyrroline-3-carbonitrile

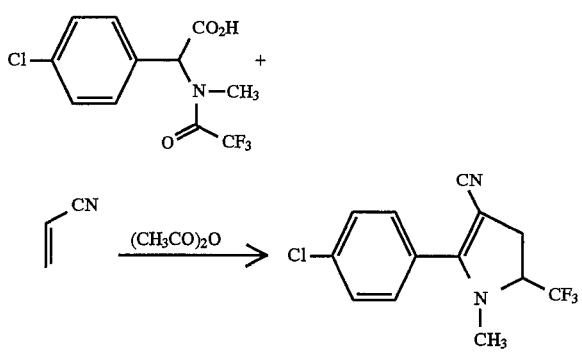

A solution of 2-(p-chlorophenyl)-N-(trifluoromethyl)sarcosine (7.4 g, 0.02 mol) in acetonitrile is treated with acetic anhydride (5.1 g, 0.05 mol), acrylonitrile (1.6 g, 0.03 mol) and 10 drops of triethylamine, heated at reflux temperature for 5½ hours, cooled and concentrated in vacuo to a red oil residue. The residue is filtered through silica-gel using 9:1 hexanes/ethyl acetate followed by mixtures of methylene chloride and ethyl acetate. The combined filtrates are concentrated in vacuo to give the title product as a red solid, 6.1 g (85% yield), identified by NMR and mass spectra analyses. A portion of the solid is recrystallized from methylene chloride to give light yellow needles, mp 158°–160° C.

EXAMPLE 7

Preparation of 2-(p-Chlorophenyl)-5-(trifluoromethyl)-2-pyrroline-3-carbonitrile

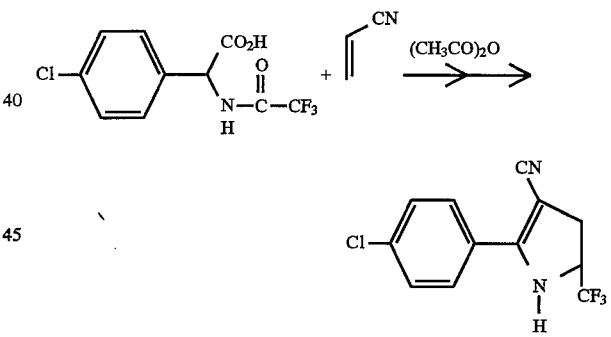

Using essentially the same procedure described in Example 6 and substituting 2-(p-chlorophenyl)-N-(trifluoroacetyl)glycine as starting material affords the title product as a light yellow solid, mp 158°–160° C.

EXAMPLE 8

Preparation of 4-Chloro-1-chloromethyl-2-(p-chlorophenyl)-5-(trifluoromethyl)pyrrole-3-carbonitrile

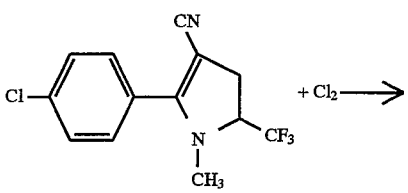

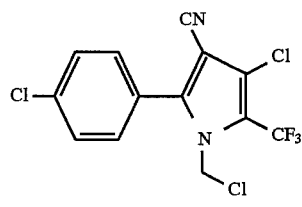

To a solution of 2-(p-chlorophenyl)-1-methyl-5-(trifluoromethyl)-2-pyrroline-3-carbonitrile (2.85 g, 0.01 mol) in o-dichlorobenzene is added chlorine (0.8 g, 0.011 mol); the resulting solution is stirred at room temperature for 1 hour, heated slowly to 90° C. over a 2 hour period, cooled to 50° C., treated with additional chlorine (0.8 g, 0.11 mol), heated at 110° C. for 24 hours, cooled to room temperature, treated with additional chlorine and concomitant additions of small portions of benzoyl peroxide and heated at 110° C. for a 4 hour period or until reaction is complete by chromatographic analysis. The resultant solution is cooled, washed with sodium metabisulfite solution and concentrated in vacuo to give a residue which is crystallized by the addition of heptane to afford the title product as a white solid, mp 107°–108° C.

EXAMPLE 9

Preparation of 4-Chloro-2-(p-chlorophenyl)-1-ethoxymethyl)-5-trifluoromethyl)pyrrole-3-carbonitrile

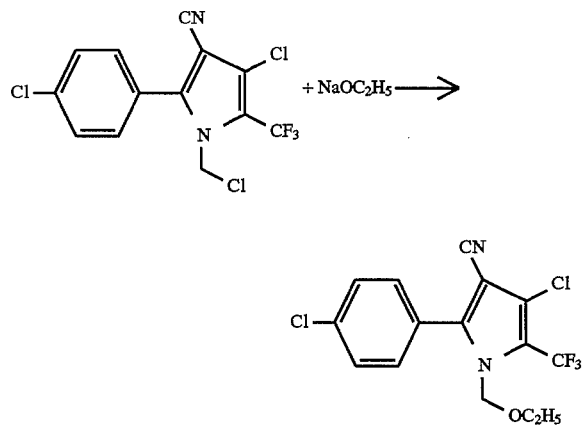

A solution of 4chloro-1-(chloromethyl)-2-(p-chlorophenyl)-5-(trifluoromethyl)pyrrole-3-carbonitrile (2.6 g, 0.0074 mol) in tetrahydrofuran is treated with sodium ethoxide as a 21% wt/wt solution in denatured ethanol (3.6 mL, 0.0096 mol), stirred at room temperature for 1 hour, treated with an additional 2–3 drops of the sodium ethoxide solution, heated at reflux temperature for 1 hour, cooled and poured into water. The resultant precipitate is filtered, dried and recrystallized from isopropanol to afford the title product as a white solid, 1.6 g (60% yield), mp 104.0°–104.5° C.

EXAMPLE 10

Preparation of 2-(p)-Chlorophenyl)-1-methyl-5-(trifluoromethyl)pyrrole-3-carbonitrile

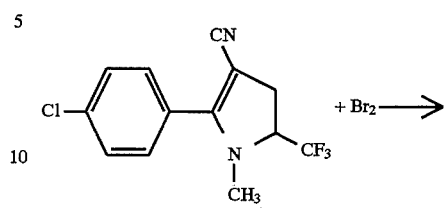

A mixture of 2-(p-chlorophenyl)-1-methyl-5-(trifluoromethyl)-2-pyrroline-3-carbonitrile (2.87 g, 0.01 mol) in chlorobenzene is treated with a solution of bromine (1.76 g, 0.011 mol) in chlorobenzene and heated at 100° C. for 4–5 hours (until the reaction is complete by HPLC analysis). The reaction mixture is cooled to room temperature, diluted with water and extracted with ethyl acetate. The organic extracts are combined, washed sequentially with water, sodium metabisulfite and water, dried over $MgSO_4$ and concentrated in vacuo to give a pale yellow solid residue. The solid is recrystallized from heptane/ethyl acetate to give the title product as pale yellow crystal, 2.4 g, (84.2% yield), mp 129.5°–130° C.

EXAMPLE 11

Preparation of 4-Bromo-2-(p)-Chlorophenyl)-1-methyl-5-(trifluoromethyl)pyrrole-3-carbonitrile

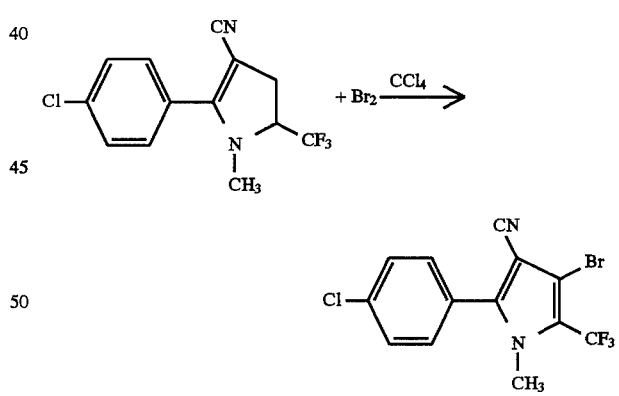

A mixture of 2-(p-chlorophenyl)-1-methyl-5-(trifluoromethyl)-2-pyrroline-3-carbonitrile (2.87 g, 0.01 mol) in carbon tetrachloride and bromine (3.2 g, 0.015 mol) is heated at reflux temperature for 2 hours, cooled to room temperature, treated with additional bromine (3.2 g, 0.015 mol), heated at reflux temperature for 6–7 hours (until reaction is complete by HPLC analysis), cooled to room temperature, washed with aqueous sodium metabisulfite and concentrated in vacuo to give a residue. The residue is recrystallized from heptane to give the title product as white crystal, mp 131°–131.5° C.

We claim:

1. A process for the preparation of a compound having the structure II

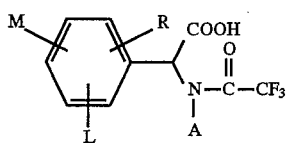

wherein

A is hydrogen or $C_1$–$C_4$ alkyl;

L is hydrogen or halogen and

M and R are each independently hydrogen, $C_1$–$C_3$ alkyl, $C_1$–$C_3$ alkoxy, $C_1$–$C_3$ alkylthio, $C_1$–$C_3$ alkylsulfinyl, $C_1$–$C_3$ alkylsulfonyl, CN, $NO_2$, halogen, $CF_3$, $R_1CF_2Z$, $R_2CO$ or $NR_3R_4$ and when M and R are on adjacent positions they may be taken together with the carbon atoms to which they are attached to form a ring in which MR represents the structure —$OCH_2O$—, —$OCF_2O$— or —CH=CH—CH=CH— with the proviso that when A is hydrogen, then at least one of L, M and R must be other than hydrogen;

Z is $S(O)_n$ or O;

$R_1$ is hydrogen, F, $CHF_2$, CHFCl or $CF_3$;

$R_2$ is $C_1$–$C_4$ alkyl, $C_1$–$C_4$ alkoxy or $NR_3R_4$;

$R_3$ is hydrogen or $C_1$–$C_4$ alkyl;

$R_4$ is hydrogen, $C_1$–$C_4$ alkyl or $R_5CO$;

$R_5$ is hydrogen or $C_1$–$C_4$ alkyl and n is an integer of 0, 1 or 2;

which consists essentially of reacting an aldehyde having the structure

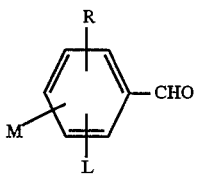

wherein L, M and R are as defined above with at lest one molar equivalent of a compound having the structure $H_2N$—A.HCl wherein A is as described above, in the presence of a solvent to form a first intermediate, reacting said first intermediate with an aqueous solution containing at least one molar equivalent of an alkali metal cyanide to form a second intermediate, extracting said second intermediate from the reaction mixture with a suitable extraction solvent, reacting said second intermediate with a lower alkyl anhydride in the presence of an organic base to form a third intermediate, reacting said third intermediate with a mineral acid in the presence of water, optionally at the reflux temperature of the solvent, to give an amino acid intermediate having the structure III

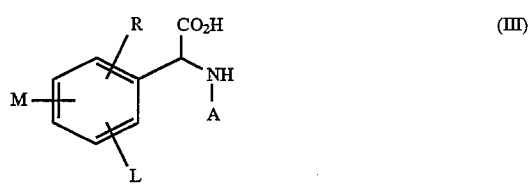

wherein A, L, M and R are as defined above; and trifluoroacetylating said amino acid intermediate with a trifluoroacetylation agent to give the desired compound having structure II.

2. The process according to claim 1 wherein A is $CH_3$, L and R are hydrogen and M is halogen.

3. The process according to claim 1 wherein A is hydrogen, L and R are hydrogen and M is halogen.

4. The process according to claim 1 wherein the trifluoroacetylation agent is trifluoroacetic anhydride.

5. The process according to claim 1 wherein A is hydrogen and the trifluoroacetylation agent is ethyl trifluoroacetate.

6. The process according to claim 5 which further comprises alkylating the compound having structure II wherein A is hydrogen with a lower alkyl halide.

7. The process according to claim 6 wherein the lower alkyl halide is methyliodide.

* * * * *

UNITED STATES PATENT AND TRADEMARK OFFICE
CERTIFICATE OF CORRECTION

PATENT NO. : 5,625,082
DATED : April 29, 1997
INVENTOR(S) : Doehner, et. al.

It is certified that error appears in the above-identified patent and that said Letters Patent is hereby corrected as shown below:

Title page, item [73], Assignee: should read --American Cyanamid Company.--

Signed and Sealed this

Thirtieth Day of June, 1998

Attest:

BRUCE LEHMAN

Attesting Officer

Commissioner of Patents and Trademarks